US006938622B2

(12) United States Patent
Huang

(10) Patent No.: US 6,938,622 B2
(45) Date of Patent: Sep. 6, 2005

(54) EARPLUG AND APPARATUS WITH THE EARPLUGS

(76) Inventor: Fu-Sheng Huang, 10F-1, No. 681, Chungjeng Rd., Chungho City, Taipei Hsien (TW)

( * ) Notice: Subject to any disclaimer, the term of this patent is extended or adjusted under 35 U.S.C. 154(b) by 0 days.

(21) Appl. No.: 10/966,306

(22) Filed: Oct. 15, 2004

(65) Prior Publication Data

US 2005/0087195 A1 Apr. 28, 2005

(30) Foreign Application Priority Data

Oct. 24, 2003 (TW) ........................................ 92129573 A

(51) Int. Cl.[7] ................................................ A61F 11/00
(52) U.S. Cl. ........................ 128/864; 128/867; 181/129; 181/135
(58) Field of Search ................................ 128/864, 865, 128/866, 867; 181/128, 129, 130, 131, 134, 135

(56) References Cited

U.S. PATENT DOCUMENTS 5,631,965 A * 5/1997 Chang et al. .................. 381/72
6,082,485 A * 7/2000 Smith .......................... 181/135

* cited by examiner

*Primary Examiner*—Henry Bennett
*Assistant Examiner*—Camtu Nguyen
(74) *Attorney, Agent, or Firm*—Dellett & Walters

(57) ABSTRACT

An earplug has an open inserting end, an open inlet end, a cover, a hollow body, a soft sheath, a tube and a sound-processing unit. The sound passes through the open inlet end, is processed by the sound-processing unit and then passes into an ear canal. Alternatively, RF (Radio Frequency) signals pass through the open inlet end and are processed by the sound-processing unit, and then radio signals pass into the ear canal. The soft sheath has a through hole. The tube is mounted through the through hole in the soft sheath and allows the open inserting end to communicate with the ambient air. Furthermore, the soft sheath and the tube are replaceable to conform to sanitary standards.

13 Claims, 6 Drawing Sheets

US 6,938,622 B2

EARPLUG AND APPARATUS WITH THE EARPLUGS

BACKGROUND OF THE INVENTION

1. Field of the Invention

The present invention relates to an earplug and an apparatus with the earplugs, and more particularly to an apparatus, wherein the earplugs are partly consisted of replaceable components and extended with additive devices two components of the apparatus.

2. Description of Related Art

People now prefer living in an environment without undesired interference. For example, some people use earplug earphones to listen to music or to make phone calls for avoiding any interference from their surroundings and improving their listening at the same time. Living or working in a noisy environment over a period of time makes a person loses efficiency, reduces his memory capability, ever anxious and increases the risk of cardiovascular disease accordingly. Some people use earphones to listen to music or make phone calls to avoid the interference from noise in their surroundings. Therefore, some people need to wear earplugs to block the some noise all the while under this circumstance.

In general, people often wear isolating earplugs made of resilient foam and insert the earplugs respectively into the ear canals. However, the isolating earplugs block the air between the inside and outside of a person's the ear canal and make the person uncomfortable after a period of wearing the earplugs.

With reference to FIGS. 1 and 2, improved earplugs (10) have been developed by NOISE Audiophone Corp. in Germany. The improved earplugs (10) effectively lower the surrounding noise and allow air to pass between the inside and outside the ear canal. The earplug (10) comprises a noise-reducing valve (12) and an insert (14) in what to be mounted the noise-reducing valve (12). The noise-reducing valve (12) is an adjustable noise-reducing valve, has an open inlet end (120) and an open outlet end (122). A passage (not shown) is defined through the noise-reducing valve (12) and communicates with the open inlet and outlet ends (120, 122). A mounting hole (140) is defined in one end of the insert (14), which abuts the noise-reducing valve (12), and allows the open outlet end (122) of the noise-reducing valve (12) to be mounted in the mounting hole (140). Another end of the insert (14) opposite to the end with the mounting hole (140) is an open inserting end (142). The open inserting end (142) has a tapered curved shape to be inserted into an ear canal. A passage (144) is defined through the insert (14) and communicates with the mounting hole (140). When the open inserting end (142) of the earplug (10) is inserted into a human ear canal, noisy sound can only pass into the open inlet end (120) of the noise-reducing valve (12) due to a seal between the insert (14) and the ear canal. The noise becomes weaker when passing through the noise-reducing valve (12) (The means for weakening the noise is implemented by tapering the cross-sectional area of the passage in the noise-reducing valve (12) to attenuate noisy sound.) and then passes through the passage (144) into the ear canal.

The earplug (10) reduces the excessive noise passing into the ear canal of a wearer and allows the wearer to still hear normal voice. In additional, the passage through the noise-reducing valve (12) cooperates with the passage (144) through the insert (14) to allow the earplug (10) to ventilate the ear canal. The pressure inside the ear canal is the same as that in the atmosphere and makes the wearer comfortable during the period of wearing the earplugs. Before manufacturing a pair of the earplugs (10), impression of the left and right ear canal of a wearer are taken respectively, and then the inserts (14) are manufactured with medical anti-allergic otoplastic or silicon material corresponding to the impression of the left and right ear canals respectively. Then, the noise-reducing valve (12) is mounted in the insert (14).

Preferably, a connectible element (16) is mounted on each of the inserts (14) and is connected to an attachment such as a cord so the attachment connects the earplugs (10) to each other. The earplugs (10) can be marked respectively with colors or characters to distinguish the right and left earplugs (10). However, the earplugs (10) must be tailor-made individually and cannot be mass-produced accordingly. A person being disturbed by noise is usually not patient with the multiple procedure and the longer lead-time of the tailor-made earplugs (10) and is hence less willing to take it. Although the earplugs (10) can help the management for the company to comply with the labor, health and safety law, it can not be a handover item of job change. The earplugs (10) will obviously increase the production costs of a company, whose employees change frequently, and a single new employee will have to repeat the whole process by all means. The earplugs have poor applicability.

SUMMARY OF THE INVENTION

The main objective of the invention is lo provide an earplug that is similar to the earplugs (10) and is available instantly so people will have it easily and without waiting.

Another objective of the invention is to provide an earplug that can act as the earplugs (10) and be mass-produced by just assembling the parts.

A further objective of the invention is to provide an earplug that is fit for the different person by just applying some replaceable elements.

An additional objective of the invention is to provide the described earplugs as an apparatus for further application in ear.

The earplug in accordance with the present invention comprises an open inserting end, an open inlet end, a hollow body, a sound-processing unit, a cover, a soft sheath, a hollow cylinder and a tube. The open inserting end is inserted into an ear canal. The open inlet end is opposite to the open inserting end.

The hollow body has a first annular sidewall and a second annular sidewall. The first annular sidewall is close to the open inlet end and has a first cavity encircled by the first annular sidewall. The second annular sidewall is close to the open inserting end and has a second cavity tapered toward the open inserting end.

The sound-processing unit is inserted through the first cavity and engages the second cavity.

The cover closes the open inlet end of the hollow body and has at least one passage. The at least one passage is defined through the cover and allows the first cavity to communicate with ambient air.

The soft sheath is mounted around the hollow body close to the open inserting end and has a bottom, a third annular sidewall, an open end and a through hole. The bottom is close to the open inserting end. The third annular sidewall is formed on the bottom and mounted around the second sidewall of the hollow body. The open end is opposite to the bottom. The through hole is defined through the bottom.

The hollow cylinder is mounted inside the second cavity close to a bottom edge of the hollow body and has a through hole.

The tube is mounted securely through the through hole in the sheath into the through hole in the hollow cylinder and allows the second cavity to communicate with the open inserting end.

The sound passing through the open inlet end is processed by the sound-processing unit and then passes into the ear canal. Furthermore, the soft sheath and the tube are replaceable to comply with sanitary standards. The sheath is made of soft material and deforms to close the ear canal when being inserted into the ear canal. Therefore, the earplug can be used by anyone at any time without ordering in advance.

The sound-processing unit can be a conventional noise-reducing valve to reduce the noisy sound.

The sound-processing unit can be a conventional electronic signal receiver to receive radio signals.

Two earplugs in conjunction with an attachment such as a cord or headband form a hearing protection apparatus or an audio earphone apparatus.

DETAILED DESCRIPTION OF PREFERRED EMBODIMENT

Other objectives, advantages and novel features of the invention will become more apparent from the following detailed description when taken in conjunction with the accompanying drawings.

Figure 1:
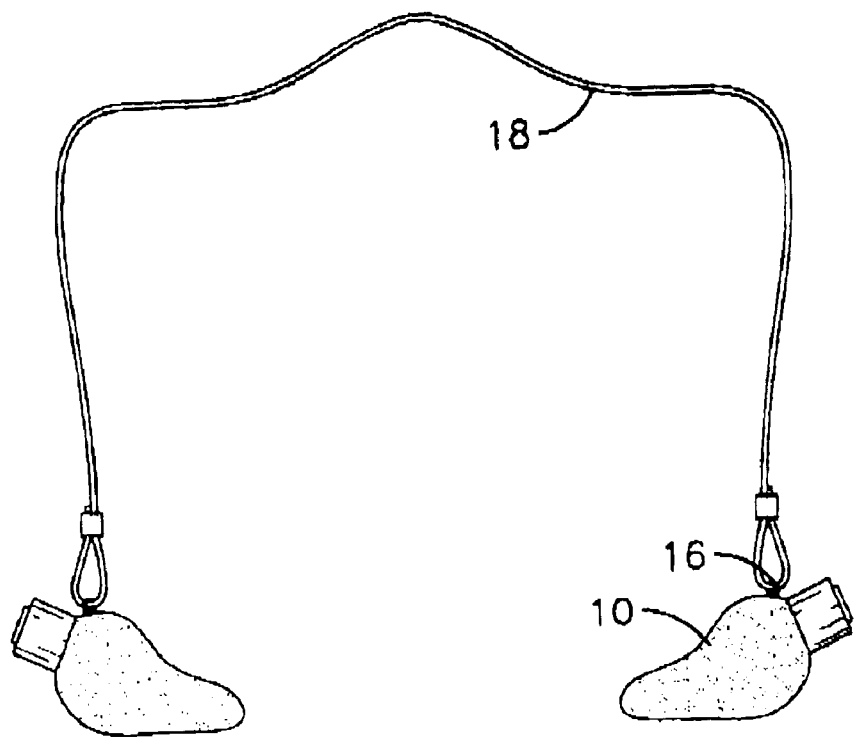
FIG. 1 is a front view of a pair of conventional earplugs in accordance with the present invention.
Figure 2:
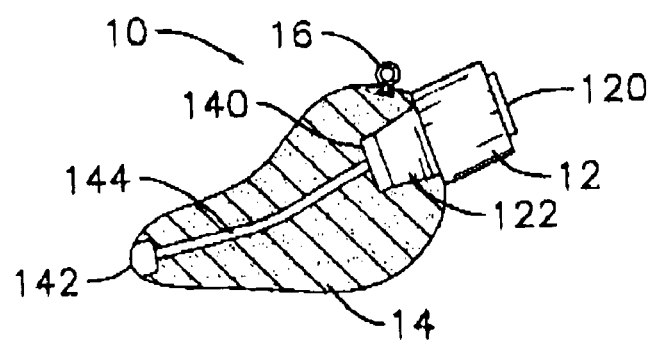
FIG. 2 is a front view of the earplug in FIG. 1.
Figure 3:
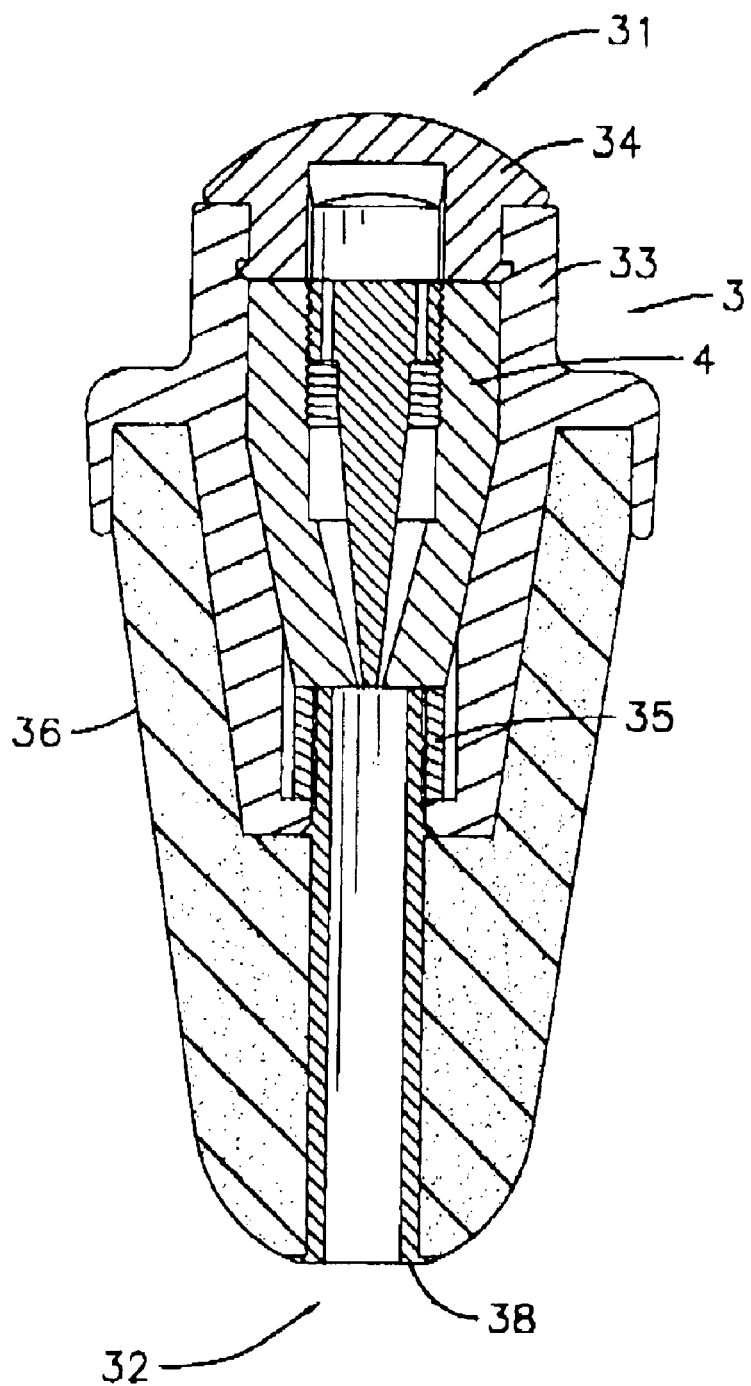
FIG. 3 is a cross-sectional side view of an earplug in accordance with the present invention.
Figure 4:
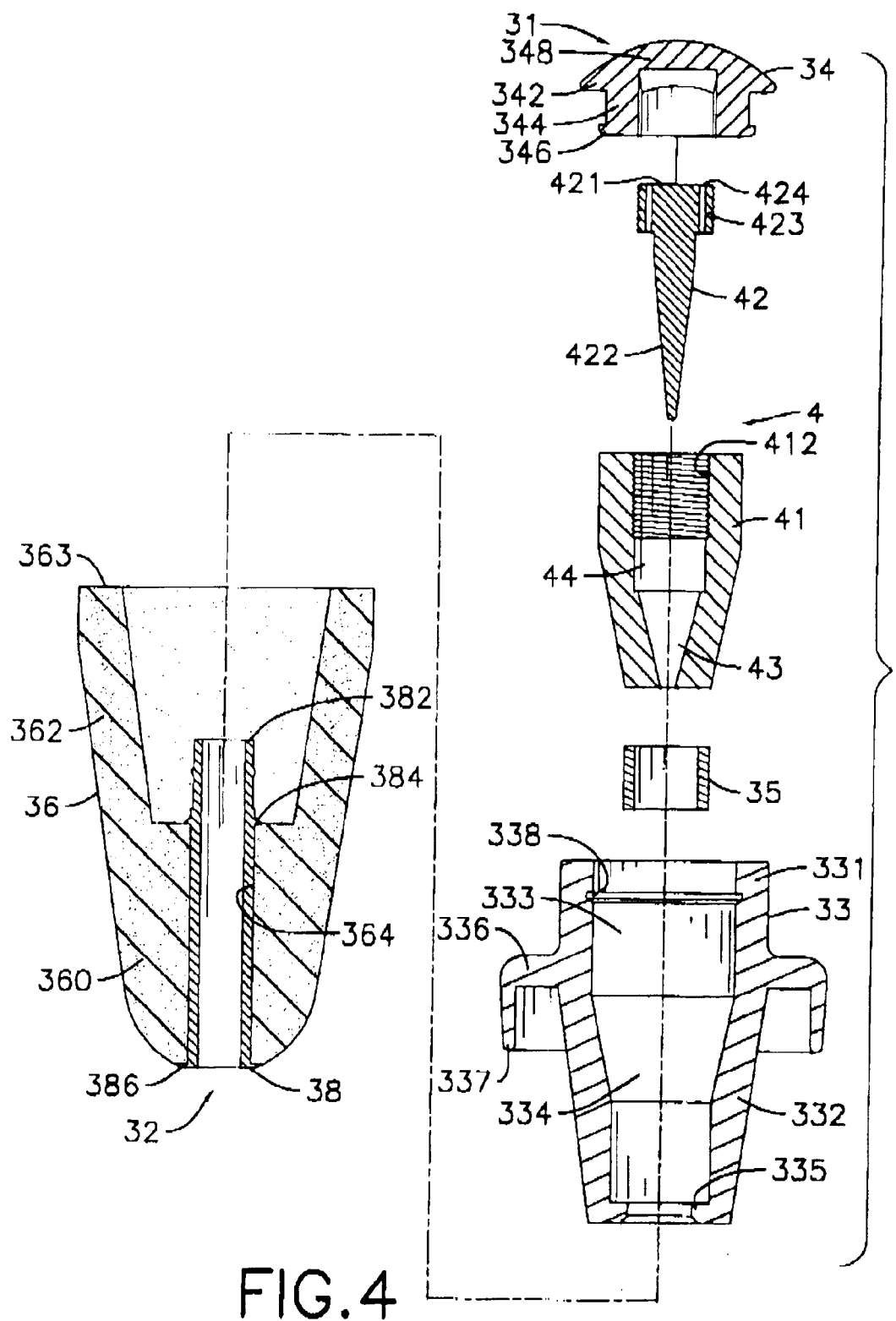
FIG. 4 is an exploded side view of the earplug in FIG. 3.

With reference to FIGS. 3 and 4, an earplug (3) in accordance with the present invention comprises an open inserting end (32) to be inserted into an ear canal and an open inlet end (31) opposite to the open inserting end (32).

The earplug (3) comprises at least a hollow body (33), a soft sheath (36) and a sound-processing unit (4) mounted in the hollow body (33).

The hollow body (33) has a first annular sidewall (331) close to the open inlet end (31). The first annular sidewall (331) has a first cavity (333) encircled by the first annular sidewall (331). The hollow body (33) has a second annular sidewall (332) close to the open inserting end (32). The second annular sidewall (332) has a second cavity (334) tapered toward the open inserting end (32). An annular groove (338) is defined in an inner surface of the first annular sidewall (331) and is described further later.

The sound-processing unit (4) is inserted through the first cavity (333) and engages the second cavity (334) by compression or bonding to each other. In an embodiment of the present invention, the sound-processing unit (4) is the noise-reducing valve developed by NOISE Audiophone Corp. in Germany. The sound-processing unit (4) has a hollow body (41) with an inner cavity (44). An inner thread (412) is formed on an inner surface of the hollow body (41) close to the open inlet end (31). The inner cavity (44) has a tapered section (43) tapered toward the open inserting end (32). A noise-reducing insert (42) has a proximal segment (421) and a distal segment (422). The distal segment (422) of the noise-reducing insert (42) extends through the inner cavity (44) into the tapered section (43). An outer thread (423) is formed on an outer surface of the proximal segment (421) and corresponds to the inner thread (412) inside the hollow body (41). A relative position of the distal segment (422) to the inner cavity (44) can be adjusted by turning the noise-reducing insert (42). The proximal segment (421) further has multiple through holes (424) defined through the proximal segment (421) and communicating with the inner cavity (44) to allow sound to pass through the through holes (424) into the inner cavity (44). The distal segment (422) is tapered. The more deeply the noise-reducing insert (42) is turned into the inner cavity (44), the less air the tapered section (43) allows to pass through and the more the sound from the open inserting end (31) to the open inserting end (32) is attenuated. Then the volume of the sound passing into the ear canal reduces. With a reverse action on the noise-reducing insert (42), the volume of the sound passing into the ear canal increases.

The soft sheath (36) is mounted around the hollow body (33) close to the open inserting end (32). The soft sheath (36) has a bottom (360) close to the open inserting end (32), a third annular sidewall (362) formed on the bottom (360) and an open end (363) opposite to the bottom (360). The third annular sidewall (362) is mounted around the second annular sidewall (332) of the hollow body (33). A through hole (364) is defined through the bottom (360).

The sound-processing unit (4) is inserted through the first cavity (333) into the second cavity (334) of the hollow body (33). The open end (363) of the soft sheath (36) is mounted around the second annular sidewall (332). Because the soft sheath (36) is soft and resilient, the soft sheath (36) deforms temporarily to adapt to and seal the inner surface of the ear canal when being inserting into the ear canal. Then the sound only passes through the open inserting end (31), is attenuated by the noise-reducing unit (4) and then enters the ear canal. In an embodiment of the earplug in accordance with the present invention, the sound-processing unit (4) is the noise-reducing valve produced by NOISE Audiophone Corp. in Germany. The position of the noise-reducing insert (42) relative to the inner cavity (44) in the noise-reducing valve is adjusted to determine a best attenuation rate of the sound for a user. The sound-processing unit (4) can be another kind of noise-reducing valve, such as a sound filter produced by the DREVE Corp. to achieve the objective of reducing noisy sound. The hollow body (33) and the soft sheath (36) can be mass-produced and are cheaper. Furthermore, the soft sheath (36) is replaceable. In all of the elements of the earplug in accordance with the present invention, the soft sheath (360) is the only element that directly contacts the inner surface of the ear canal. Thus, the cleanliness of the soft sheath (36) is important. The best way to keep the ear plug sanitary is by replacing the original sheath (36) with a new one after the original sheath (36) is soiled or has been used, and the replacement of the soft sheath (36) has low cost. The soft sheath (36) is made of medical resilient PU material (can also be made of other resilient material deforming with pressure and recovering when the pressure is released). The medical resilient PU material has soft and deformable characteristics to make the open inserting end (32) close the ear canal after being inserted into the ear canal and deform to be adapted to different people. Therefore, the earplug is available for anyone at any time without ordering in advance.

An embodiment of the earplug (3) in accordance with the present invention has the hollow body (33) having an annular flange (336). The annular flange (336) is formed around an outer surface of the hollow body (33) and abuts the open end (363) of the soft sheath (36). When the open inserting end (32) is pushed into the ear canal, the annular flange (336) pushes the sheath (360) into the ear canal. Preferably, a fourth annular sidewall (337) is formed on an outer edge of the annular flange (336) and extends toward the open inserting end (32) to cover the open end (363) of the soft sheath (360). When inserting the earplug into the ear canal, pressing the fourth annular sidewall (337) with fingers makes the insertion of the earplug easier.

Figure 5:
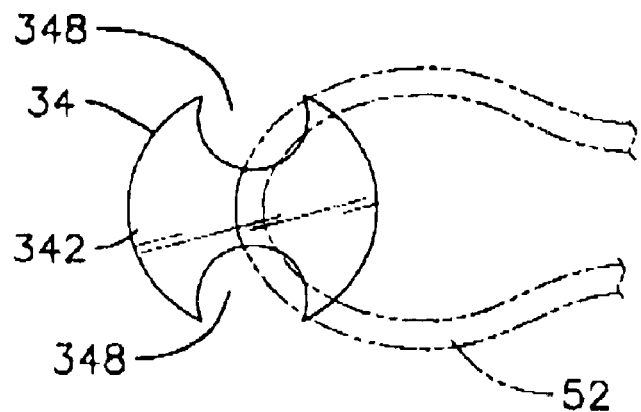
FIG. 5 is an enlarged rear view of a cord attached to a cover of the earplug in FIG. 3.

Another embodiment of the earplug (3) in accordance with the present invention has a cover (34) to protect the sound-processing unit (4) in the hollow body (33). The cover (34) closes the open inlet end (31) of the hollow body (33). The cover (34) has a cap (342) having at least one passage (348) (as shown in FIG. 5). The at least one passage (348) is defined through the cap (348) and allows the first cavity (333) to communicate with ambient air. A short annular sidewall (344) is formed on the cap (34) and extends toward the first cavity (333). An outer surface of the annular short sidewall (344) hermetically contacts an inner surface of first annular sidewall (331). Preferably, an annular rib (346) is formed on the outer surface of the short annular sidewall (344) and engages the annular groove (338) in the first annular sidewall (333) to strengthen the combination of the cover (34) and the hollow body (33).

Another embodiment of the earplug (3) in accordance with the present invention has a tube (38) mounted securely through the through hole (364) in the soft sheath (36). The tube (38) is harder than the sheath (36) to assure that the second cavity (334) communicates with the open inserting end (32). The secure combination of the tube (38) and the sheath (36) prevents the tube (38) from protruding out of the sheath (36). Because the open inserting end (32) on the bottom (360) of the sheath (36) extends into the ear canal, the tube (38) protruding from the open inserting end (32) would possibly injure the inner surface of the ear canal. An annular lip (386) is formed on the outer surface of the tube (38) and abuts a bottom outer edge of the through hole (364). The tube (38) has an extension section (382) extending into the second cavity (334). An annular blocking rib (384) is formed on the outer surface of the tube (38) and is described further later.

An adhesive provided by National Starch & Chemical Co., Ltd. is used to combine the sheath (36) and the tube (38). The adhesive has an appropriate stickiness and is sanitary for a human body. (The adhesive does not have heavy metal and result in over-sensitivity.) National Starch & Chemical Co., Ltd. is a member of the ICI group.

Another embodiment of the earplug (3) in accordance with the present invention has a hollow cylinder (35). An inner flange (335) is formed on a bottom edge of the hollow body (33) inside the second cavity (334) and extends inward. The hollow cylinder (35) is mounted inside the second cavity (334), abuts the inner flange (335), is located close to the through hole (364) in the soft sheath (36) and is opposite to the open inserting end (32). The hollow cylinder (35) allows the extension section (382) of the tube (38) to engage a through hole of the hollow cylinder (35). The annular blocking rib (384) hermetically abuts a top outer edge of the through hole (364) of the soft sheath (36). The hollow cylinder (35) is harder than the tube (38) so that the tube (38) deforms slightly to abut hermetically on the inner surface of the hollow cylinder (35) when the tube (38) extends into the hollow cylinder (35). The combination of the tube (38) and the hollow cylinder (35) makes the hollow body (33) and the sheath (36) engage tightly with each other and increases the hermetic seal between the sheath (38) and the hollow body (38) so the sound can only pass through the tube (38) into the ear canal. Furthermore, the tube (38) engages tightly in the through hole (364) so that the sheath (36) can be inserted easily into the ear canal by pressing the fourth annular sidewall (337) to press the hollow body (33), the hollow cylinder (35) and the tube (38).

Figure 6:
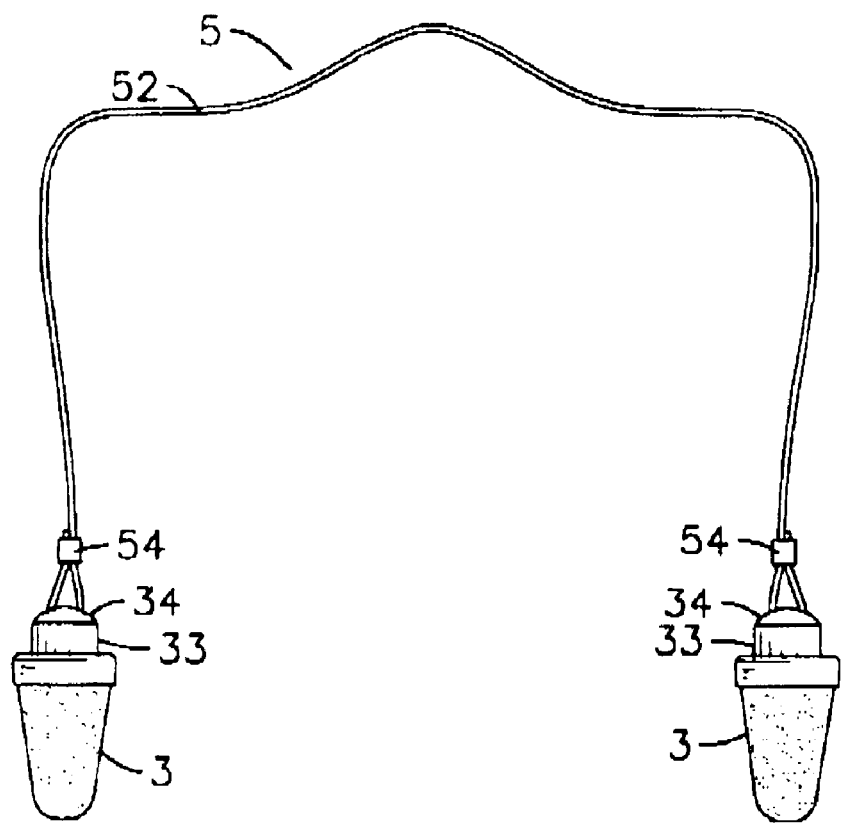
FIG. 6 is a front view of an attachment and the pair of earplugs in accordance with the present invention.

With reference to FIGS. 5 and 6, an embodiment of an apparatus with the earplugs in accordance with the present invention has an attachment (5) and two earplugs. The number of the passage (348) in the cover (34) is two. The passages (348) are defined through the cover (34) and communicate with and are opposite to each other. The opposite passages (348) not only provide ventilation but also allow the attachment (5) to pass through the passages (348). In the embodiment of the present invention, the attachment (5) is connected between the two earplugs and has a cord (52) and two clamps (54). The cord (52) has two ends extending through the passages (348) respectively in the covers (34). The clamps (54) respectively bind the ends to the cord (52) itself. The combination of the cord (52), the top covers (34) and the hollow bodies (33) makes the apparatus with earplugs in accordance with the present invention for single user.

Figure 7:
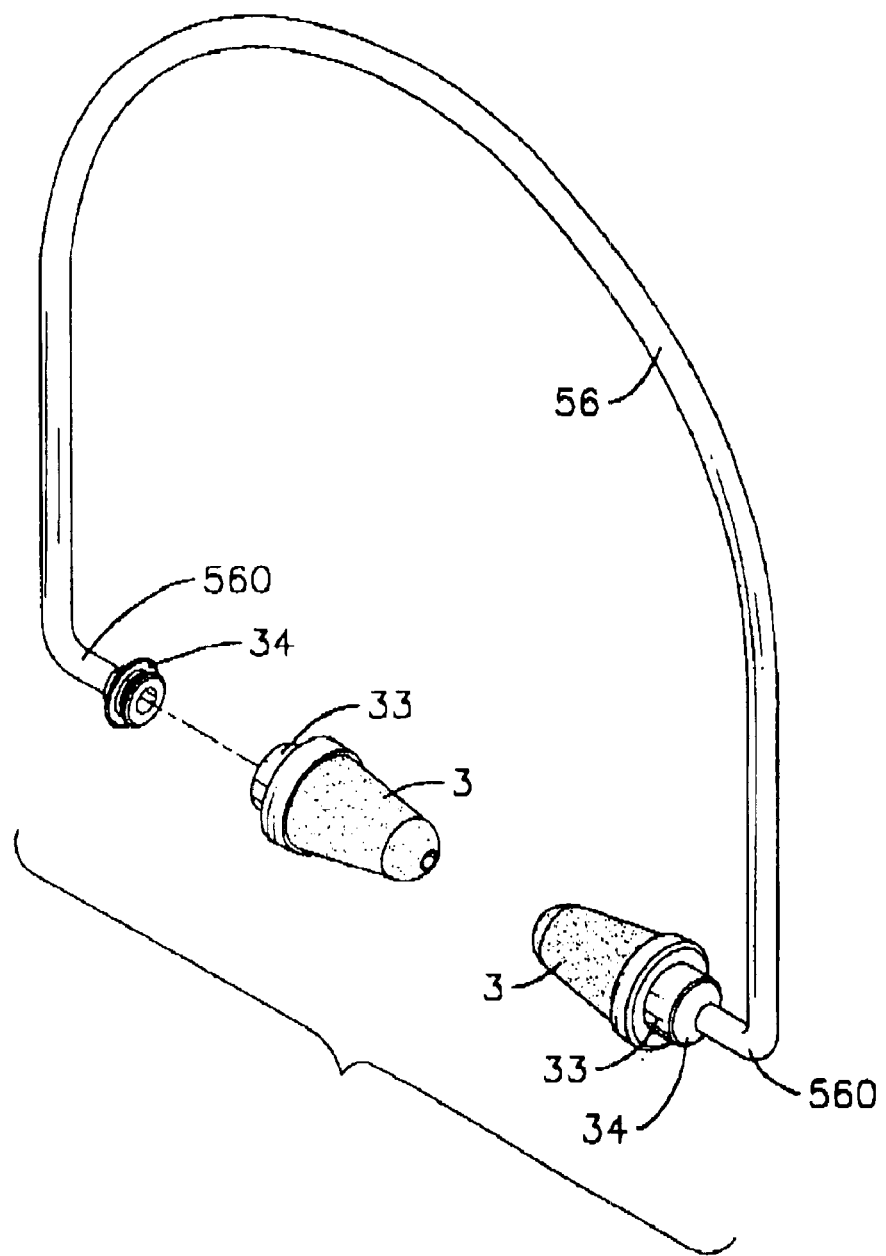
FIG. 7 is a perspective view of another attachment and the pair of earplugs in accordance with the present invention.

With reference to FIG. 7, another embodiment of the apparatus with the earplugs in accordance with the present invention has the attachment (5) has a U-shaped headband (56) and electric earphones. The headband (56) has two ends (560) is integrally formed respectively on the covers (34). Then the covers (34) are mounted respectively in the hollow bodies (33) to make the apparatus with earplugs in accordance with the present invention for a single user.

Figure 8:
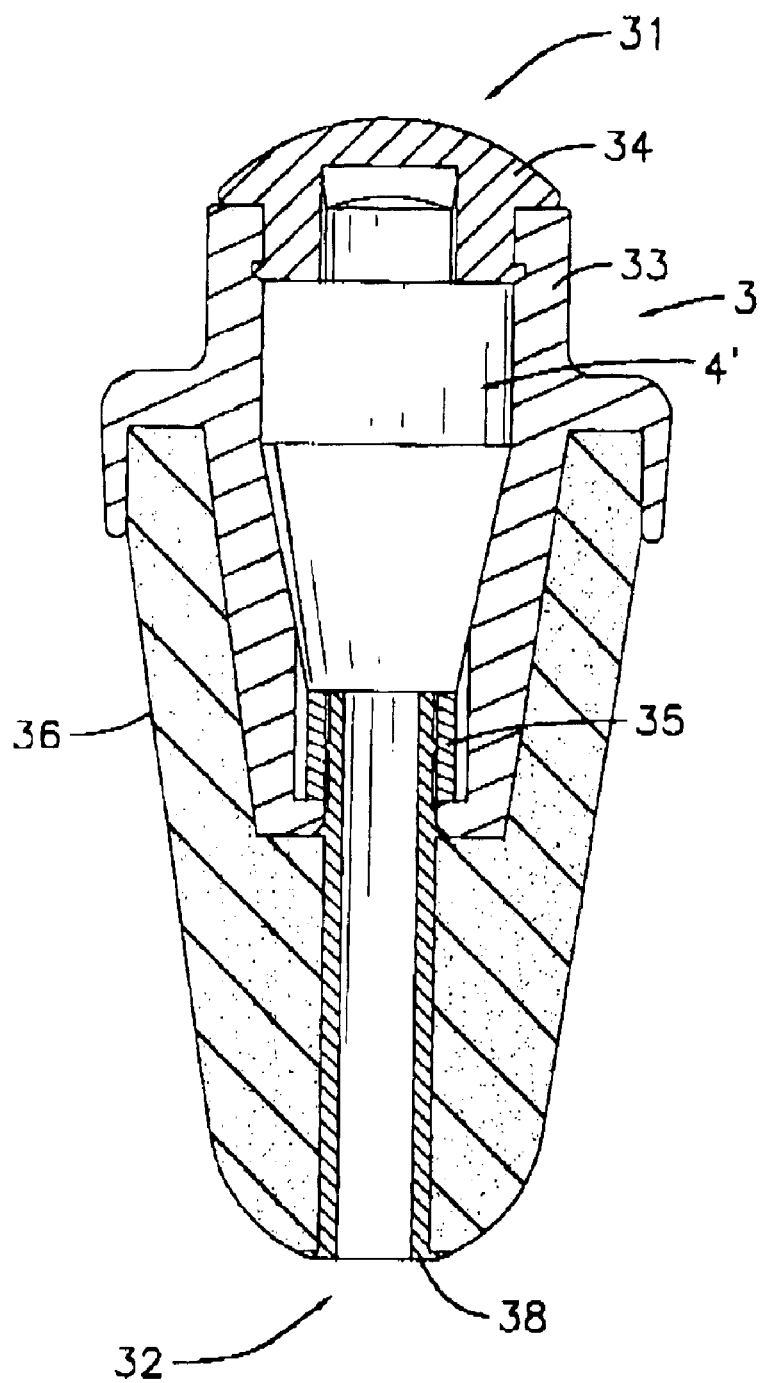
FIG. 8 is a set of block diagrams of the hollow body, electronic signal receiver, cover, soft sheath, hollow cylinder and tube in FIG. 3.

With reference to FIGS. 6 and 7, the apparatus with the earplugs (3) in accordance with the present invention will be a hearing protection apparatus if the sound-processing unit (4) (as shown in FIG. 3) of the earplug (3) is a noise-reducing valve. With reference FIG. 8, the apparatus with the earplug in accordance with the present invention will be an audio earphone apparatus if the sound-processing unit (4') is a conventional electronic signal receiver for receiving radio signals.

Even though numerous characteristics and advantages of the present invention have been set forth in the foregoing description, together with details of the structure and function of the invention, the disclosure is illustrative only. Changes may be made in detail, especially in matters of shape, size, and arrangement of parts within the principles of the invention to the full extent indicated by the broad general meaning of the terms in which the appended claims are expressed.

What is claimed is:

1. An earplug comprising:
   an open inserting end;
   an open inlet end opposite to the open inserting end;
   a hollow body having
      a first annular sidewall close to the open inlet end and having a first cavity encircled by the first annular sidewall; and
      a second annular sidewall close to the open inserting end and having a second cavity tapered toward the open inserting end;
   a sound-processing unit inserted through the first cavity and engaging the second cavity; and
   a soft sheath mounted around the hollow body close to the open inserting end and having
      a bottom close to the open inserting end;
      a third annular sidewall formed on the bottom and mounted around the second annular sidewall of the hollow body;
      an open end opposite to the bottom; and
      a through hole defined through the bottom.

2. The earplug as claimed in claim 1, wherein the hollow body has an annular flange formed around an outer surface of the hollow body and abutting the open end of the soft sheath; and a fourth annular sidewall formed on an outer edge of the annular flange and extending toward the open inserting end to cover the open end of the soft sheath.

3. The earplug as claimed in claim 1 further comprising a cover closing the open inlet end of the hollow body and having
at least one passage defined through the cover and allowing the first cavity to communicate with ambient air.

4. The earplug as claimed in claim 3, wherein:
an annular groove is defined in an inner surface of the first annular sidewall;
the cover has
a cap having at least one passage defined through the cap;
a short annular sidewall is formed on the cap and extends toward the first cavity and has
an outer surface hermetically contacting an inner surface of first annular sidewall; and
an annular rib formed on the outer surface of the short annular sidewall and engaging the annular groove of the first annular sidewall to strengthen the combination of the cover and the hollow body.

5. The earplug as claimed in claim 1 further comprising a tube mounted securely through the through hole in the soft sheath and allowing the second cavity to communicate with the open inserting end.

6. The earplug as claimed in claim 5 further comprising:
an inner flange formed on a bottom edge of the hollow body inside the second cavity and extending inward;
a hollow cylinder, mounted inside the second cavity, abutting the inner flange, located close to the through hole in the soft sheath and opposite to the open inserting end and allowing an extension section of the tube to engage a through hole in the hollow cylinder; and
an annular blocking rib formed on the outer surface of the extension section of the tube and hermetically abutting a top outer edge of the through hole in the soft sheath.

7. The earplug as claimed in claim 1, wherein the soft sheath is made of medical resilient material.

8. The earplug as claimed in claim 1, wherein the sound-processing unit is a noise-reducing valve.

9. The earplug as claimed in claim 1, wherein the sound-processing unit is an electronic signal receiver for receiving radio signals.

10. A hearing protection apparatus with earplugs comprising:
two earplugs and each earplug having
an open inserting end;
an open inlet end opposite to the open inserting end;
a hollow body having
a first annular sidewall close to the open inlet end and having a first cavity encircled by the first annular sidewall; and
a second annular sidewall close to the open inserting end and having a second cavity tapered toward the open inserting end;
a sound-processing unit inserted through the first cavity and engaging the second cavity, wherein the sound-processing unit is a noise-reducing valve;
a cover closing the open inlet end of the hollow body and having
at least one passage defined through the cover and allowing the first cavity to communicate with ambient air;
a soft sheath mounted around the hollow body close to the open inserting end and having a bottom close to the open inserting end;
a third annular sidewall formed on the bottom and mounted around the second sidewall of the hollow body;
an open end opposite to the bottom; and
a through hole defined through the bottom;
a hollow cylinder mounted inside the second cavity close to a bottom edge of the hollow body and having a through hole; and
a tube mounted securely through the through hole in the soft sheath into the through hole in the hollow cylinder and allowing the second cavity to communicate with the open inserting end; and
an attachment connected between the earplugs.

11. The hearing protection apparatus with earplugs as claimed in claim 10, wherein
the number of the passages is two, and the passages are defined through the cover, communicate with and are opposite to each other; and
the attachment has
a cord having two ends extending through the passages respectively in the covers; and
two clamps respectively binding the ends to the cord itself.

12. The hearing protection apparatus with earplugs as claimed in claim 10, wherein the attachment is a U-shaped headband having two ends integrally formed respectively on the covers.

13. An audio earphone apparatus with earplugs electrically connected to an audio device and comprising:
two earplugs, and each earplug having
an open inserting end;
an open inlet end opposite to the open inserting end;
a hollow body having
a first annular sidewall close to the open inlet end and having a first cavity encircled by the first annular sidewall; and
a second annular sidewall close to the open inserting end and having a second cavity tapered toward the open inserting end;
a sound-processing unit inserted through the first cavity and engaging the second cavity, wherein the sound-processing unit is an electronic signal receiver;
a cover closing the open inlet end of the hollow body and having
at least one passage defined through the cover and allowing the first cavity to communicate with ambient air;
a soft sheath mounted around the hollow body close to the open inserting end and having
a bottom close to the open inserting end;
a third annular sidewall formed on the bottom and mounted around the second sidewall of the hollow body;
an open end opposite to the bottom; and
a through hole defined through the bottom;
a hollow cylinder mounted inside the second cavity, abutting the inner flange and having a through hole; and
a tube mounted securely through the through hole in the soft sheath into the through hole in the hollow cylinder and allowing the second cavity to communicate with the open inserting end; and
an attachment connected between the earplugs.

* * * * *